United States Patent [19]

Stetter et al.

[11] 4,391,626
[45] Jul. 5, 1983

[54] HALOALKYLAMIDE COMPOUNDS AND HERBICIDAL ANTIDOTE COMPOSITIONS

[75] Inventors: Jörg Stetter; Wolf Reiser, both of Wuppertal; Wilfried Faust, Odenthal, all of Fed. Rep. of Germany

[73] Assignee: Bayer Aktiengesellschaft, Leverkusen, Fed. Rep. of Germany

[21] Appl. No.: 226,287

[22] Filed: Jan. 19, 1981

[30] Foreign Application Priority Data

Feb. 9, 1980 [DE] Fed. Rep. of Germany ....... 3004871

[51] Int. Cl.³ .................... A01N 37/00; A01N 37/18; C07C 103/44
[52] U.S. Cl. .................................... 71/88; 71/90; 71/92; 71/94; 71/95; 71/98; 71/100; 71/118; 564/209; 564/212
[58] Field of Search .................... 564/209, 212; 71/98, 71/100, 118, 88, 90, 92, 94, 95

[56] References Cited

U.S. PATENT DOCUMENTS 3,867,444 2/1975 Baker .................................. 564/209
3,976,471 8/1976 Richter et al. ................. 564/212 X
4,033,756 7/1977 Hoffman ........................ 564/209 X
4,195,036 3/1980 Gozzo et al. ....................... 564/209
4,260,410 4/1981 Schinski et al. ................ 564/214 X

FOREIGN PATENT DOCUMENTS 10715 of 0000 European Pat. Off. .
2218097 of 0000 Fed. Rep. of Germany .
2726253 of 0000 Fed. Rep. of Germany .

Primary Examiner—Thomas A. Waltz
Attorney, Agent, or Firm—Felfe & Lynch

[57] ABSTRACT

New halogenoalkylamides of the general formula

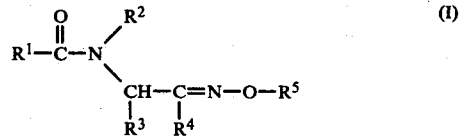

in which
$R^1$ represents halogenoalkyl,
$R^2$ represents alkyl, alkenyl, alkynyl, alkoxyalkyl, alkylthioalkyl, aralkyl, halogenoalkyl or alkoximinoalkyl,
$R^3$ represents hydrogen or alkyl with 1 to 4 carbon atoms,
$R^4$ represents hydrogen or alkyl with 1 to 4 carbon atoms and
$R^5$ represents hydrogen, alkyl, alkenyl, alkynyl or aralkyl, processes for their preparation and their use as antidotes for protecting crop plants from damage by herbicidally effective thiolcarbamates and acetanilides.

Novel amine derivatives of the general formula

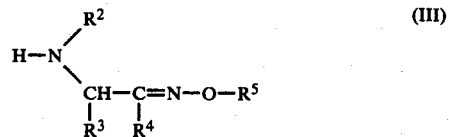

in which $R^2$, $R^3$, $R^4$ and $R^5$ have the above-mentioned meaning, and a process for their preparation.

A novel halogenoacylamines of the general formula

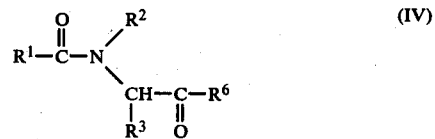

in which
$R^1$, $R^2$ and $R^3$ have the above-mentioned meaning and
$R^6$ represents hydrogen or methyl, as well as processes for their preparation.

42 Claims, No Drawings

HALOALKYLAMIDE COMPOUNDS AND HERBICIDAL ANTIDOTE COMPOSITIONS

This invention relates to certain new haloalkylamide compounds. Further, the invention relates to methods of using such compounds as antidotes for protecting crop plants from damage by herbicidally active thiolcarbamates and acetanilides. The present invention also relates to new compositions containing said compounds as active antidotal ingredients, together with certain herbicidally active thiolcarbamates or acetanilides.

By "antidotes" ("safeners") there are to be understood, in the present connection, substances which are capable of specifically antagonising harmful effects of herbicides on crop plants, that is to say of protecting the crop plants without thereby noticeably influencing the herbicidal action on the weeds to be combated.

It is known that when certain thiolcarbamates and acetanilides are used for combating weeds in maize and other crops, they cause damage, to a greater or lesser extent, to the crop plants. It is furthermore known that such compounds as, for example, N,N-di-n-propyl-dichloroacetamide are suitable for reducing damage caused to crop plants by thiolcarbamates or acetanilides (see DE-OS (German Published Specification) No. 2,218,097). However, the activity of this substance as an antidote is not always completely satisfactory.

The present invention now provides, as new compounds, the halogenoalkylamides of the general formula

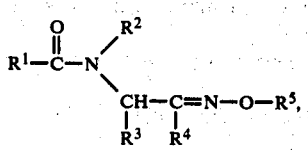

in which
- $R^1$ represents halogenoalkyl,
- $R^2$ represents alkyl, alkenyl, alkynyl, alkoxyalkyl, alkylthioalkyl, aralkyl, halogenoalkyl or alkoximinoalkyl,
- $R^3$ represents hydrogen or alkyl with 1 to 4 carbon atoms,
- $R^4$ represents hydrogen or alkyl with 1 to 4 carbon atoms and
- $R^5$ represents hydrogen, alkyl, alkenyl, alkynyl or aralkyl.

The invention also provides a process for the preparation of a halogenoalkylamide of the formula (I) in which
(a) an acid chloride or acid anhydride of the general formula

in which
$R^1$ has the meaning indicated above and
X represents chlorine or the radical $R^1$—CO—O—, wherein $R^1$ again has the meaning indicated above, is reacted with an amine derivative of the general formula

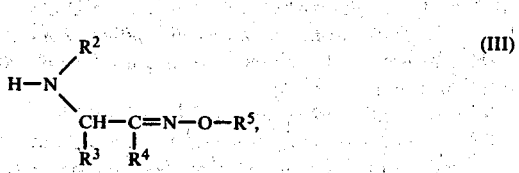

in which $R^2$, $R^3$, $R^4$ and $R^5$ have the meanings indicated above, if appropriate in the presence of an acid-binding agent and if appropriate in the presence of an inert diluent, or (b) a halogenoacylamine of the general formula

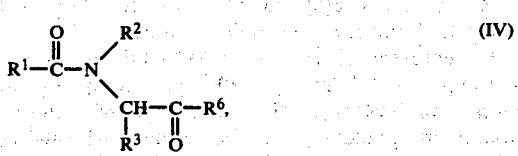

in which
$R^1$, $R^2$ and $R^3$ have the meanings indicated above and
$R^6$ represents hydrogen or methyl,
is reacted with an hydroxylamine derivative of the general formula

in which $R^5$ has the meaning indicated above, in the presence of an acid-binding agent and in the presence of a diluent.

It has been found that halogenoalkylamides of the formula (I) are outstandingly suitable for use for protecting crop plants from damage by herbicidally active thiolcarbamates or by herbicidally active acetanilides.

It has also been found that the new active compound combinations consisting of a halogenoalkylamide of the formula (I) and at least one herbicidally active thiolcarbamate and/or at least one herbicidally active acetanilide are outstandingly suitable for selectively combating weeds in crops of useful plants.

Surprisingly, herbicidal damage to crop plants by thiolcarbamates or by acetanilides can be better suppressed if halogenoalkylamides of the formula (I) are also used than if the known compound N,N-di-n-propyl-dichloroacetamide, which is a chemically similar substance of the same type of action, is used. Moreover, it was not to be expected that the active compound combinations according to the invention have better selective herbicidal properties than active compound combinations which consist of at least one herbicidally active thiolcarbamate or at least one herbicidally active acetanilide and N,N-di-n-propyl-dichloroacetamide which is known as an antidote.

The formula (I) provides a general definition of the halogenoalkylamides according to the invention. Preferably, in this formula,
$R^1$ represents straight-chain or branched halogenoalkyl with 1 to 4 carbon atoms and 1 to 3 halogen atoms (especially chlorine and/or bromine atoms),
$R^2$ represents straight-chain or branched alkyl with 1 to 6 carbon atoms, alkenyl with up to 6 carbon atoms, alkynyl with up to 6 carbon atoms, alkoxyalkyl with 1 to 4 carbon atoms in the alkoxy part, alkylthioalkyl with 1 to 4 carbon atoms in the alkyl part and 1 to 4 carbon atoms in the alkylthio part, aralkyl with 6 to 10 carbon atoms in the aryl part and 1 to 4 carbon atoms in the alkyl part, halogenoalkyl with 1 to 6 carbon atoms and 1 to 5 halogen atoms or alkoximinoalkyl with 1 to 4 carbon atoms in the alkoxy group and 1 or 2 carbon atoms in the alkyl group, $R^3$ represents hydrogen, methyl or ethyl, $R^4$ represents hydrogen, methyl or ethyl, and $R^5$ represents hydrogen, straight-chain or branched alkyl with 1 to 6 carbon atoms, alkenyl with up to 6 carbon atoms, alkynyl with up to 6 carbon atoms or aralkyl with 6 to 10 carbon atoms in the aryl part and 1 to 4 carbon atoms in the alkyl part.

Particularly preferred compounds of the formula (I) are those in which $R^1$ represents halogenoalkyl with 1 to 3 carbon atoms and 1 to 3 chlorine or bromine atoms, $R^2$ represents alkyl with 1 to 4 carbon atoms, alkenyl with up to 4 carbon atoms, alkynyl with up to 4 carbon atoms, alkoxyalkyl with 1 to 3 carbon atoms in the alkoxy group and 1 to 4 carbon atoms in the alkyl part, alkylthioalkyl with 1 to 3 carbon atoms in the alkylthio part and 1 to 3 carbon atoms in the alkyl part, aralkyl with 6 to 10 carbon atoms in the aryl part and 1 or 2 carbon atoms in the alkyl part, halogenoalkyl with 1 to 4 carbon atoms and 1 to 3 halogen atoms selected from fluorine, chlorine and bromine atoms, or alkoximinoalkyl with 1 to 3 carbon atoms in the alkoxy group and 1 or 2 carbon atoms in the alkyl group, $R^3$ represents hydrogen, methyl or ethyl, $R^4$ represents hydrogen, methyl or ethyl and $R^5$ represents hydrogen, alkyl with 1 to 4 carbon atoms, alkenyl with up to 4 carbon atoms, alkynyl with up to 4 carbon atoms or aralkyl with 6 to 10 carbon atoms in the aryl part and 1 or 2 carbon atoms in the alkyl part.

If dichloroacetic acid chloride and allyl-2-methoximinoethyl-amine are used as starting substances, the course of process variant (a) can be represented by the following equation:

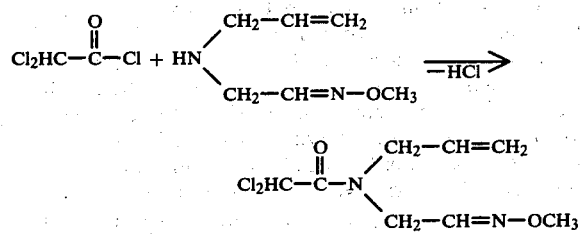

If N-2-oxopropyl-N-allyl-dichloroacetic acid amide and O-methyl-hydroxylamine hydrochloride are used as starting substances, the course of process variant (b) can be represented by the following equation:

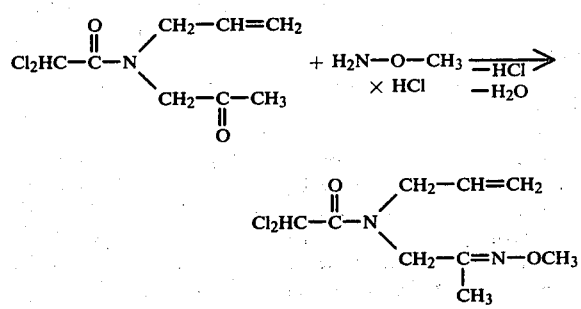

The formula (II) provides a general definition of the acid chlorides or acid anhydrides required as starting substances in process variant (a). In this formula, $R^1$ preferably has those meanings which have already been mentioned as preferred for $R^1$ in connection with the description of the halogenoalkylamides of the formula (I). X preferably represents chlorine or the radical $R^1$—CO—O, $R^1$ in turn preferably having those meanings which have already been mentioned above as preferred for $R^1$.

The acid chlorides and acid anhydrides of the formula (II) are known, or they can be prepared by known methods.

The formula (III) provides a general definition of the amine derivatives also required as starting substances in process variant (a). In this formula, $R^2$, $R^3$, $R^4$ and $R^5$ preferably have those meanings which have already been mentioned as preferred in connection with the description of the halogenoalkylamides of the formula (I).

The amine derivatives of the general formula

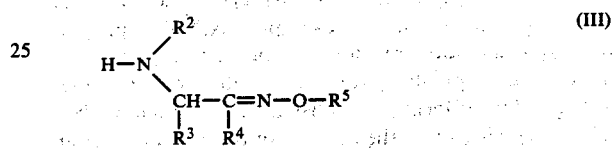

in which $R^2$ represents alkyl, alkenyl, alkynyl, alkoxy-alkyl, alkylthioalkyl, aralkyl, halogenoalkyl or alkoximinoalkyl, $R^3$ represents hydrogen or alkyl with 1 to 4 carbon atoms, $R^4$ represents hydrogen or alkyl with 1 to 4 carbon atoms and $R^5$ represents hydrogen, alkyl, alkenyl, alkynyl, or aralkyl, have not hitherto been disclosed in the literature.

The amine derivatives of the formula (III) can be prepared by a process in which amines of the general formula

in which $R^2$ has the meaning indicated above, are reacted with compounds of the formula

in which $R^3$, $R^4$ and $R^5$ have the meanings indicated above and Y represents halogen, tosyl or mesyl, if appropriate in the presence of an acid-binding agent and if appropriate in the presence of an inert diluent.

The formula (VI) provides a general definition of the amines required as starting substances in the preparation of the amine derivatives of the formula (III) by the above process. In formula (VI), $R^2$ preferably has those meanings which have already been mentioned as preferred for $R^2$ in connection with the description of the halogenoalkylamides of the formula (I).

The amines of the formula (VI) are known, or they can be prepared by known processes.

Some of the compounds of the formula (VII) also required as starting substances in the preparation of the amine derivatives of the formula (III) are known. The substances of the formula (VII) which have not hitherto been described in the literature, however, are prepared in a simple manner. Thus, (α) compounds of the formula (VII) are obtained by a process in which carbonyl compounds of the general formula

in which $R^3$, $R^4$ and Y have the meanings indicated above, are reacted with hydroxylamine derivatives of the general formula

in which $R^5$ has the meaning indicated above, in the presence of an acid-binding agent, for example sodium carbonate, potassium carbonate or sodium bicarbonate, and in the presence of a diluent, for example ethanol or water, at temperatures between $-20°$ C. and $100°$ C., or (β) those compounds of the formula (VII) in which Y presents bromine are obtained by a process in which compounds of the general formula

in which $R^3$, $R^4$ and $R^5$ have the meanings indicated above, are reacted with N-bromosuccinimide, of the formula

in the presence of a diluent, for example carbon tetrachloride, at temperatures between $20°$ C. and $80°$ C.

The substances of the formulae (V), (VIII), (IX) and (X) required as starting materials in the preparation of the compounds of the formula (VII) by process variants (α) and (β) are known, or they can be prepared in a simple manner by processes which are known in principle.

Acid-binding agents which can be used in the preparation of the amine derivatives of the formula (III) by the process indicated above are any of the customary acid acceptors. These include, as preferences, alkali metal hydroxides, such as sodium hydroxide and potassium hydroxide, alkali metal carbonates, such as sodium carbonate, potassium carbonate and sodium bicarbonate, and lower tertiary amines, such as triethylamine, dimethylbenzylamine, pyridine, diazabicyclooctane and 1,8-diaza-bicyclo[5.4.0]undec-7-ene. However, the amine of the formula (VI) when employed in excess can also simultaneously function as the acid-binding agent. In this case, it is not necessary to add an additional acid-binding agent.

The process for the preparation of the amine derivatives of the formula (III) is preferably carried out in the presence of a diluent. Diluents which can be used here are water or organic solvents, such as ether, toluene or alcohols, for example methanol or ethanol, or also the amine employed, of the formula (VI), itself.

The reaction temperatures can be varied within a substantial range in the preparation of the amine derivatives of the formula (III) by the process described above. In general, the reaction is carried out at temperatures between $-20°$ C. and $-100°$ C., preferably between $20°$ C. and $80°$ C.

In carrying out the process for the preparation of the amine derivatives of the formula (III), 1 to 3 moles of amine of the formula (VI) and, if appropriate, 1 mole of acid-binding agent are preferably employed per 1 mole of a compound of the formula (VII). Isolation of the reaction products is effected by customary methods.

In general, a procedure is followed in which, when the reaction has ended, the reaction mixture is filtered and, if appropriate after prior concentration, the filtrate is distilled or, if a solid remains, the residue is recrystallised.

Possible acid-binding agents in process variant (a) are any of the customary acid acceptors. These include, as preferences, those acid acceptors which have already been mentioned as preferred acid-binding agents in connection with the description of the process for the preparation of the amine derivatives of the formula (III). However, the amine of the formula (III) when employed in excess can also simultaneously function as the acid-binding agent.

Process variant (a) is preferably carried out in the presence of a diluent. Diluents which can be used here are any of the inert organic solvents. These include, as preferences, those solvents which have already been mentioned as preferred diluents in connection with the description of the process for the preparation of the amine derivatives of the formula (III).

The reaction temperatures can be varied within a substantial range in process variant (a). In general, the reaction is carried out at temperatures between $-20°$ C. and $+100°$ C., preferably between $0°$ C. and $80°$ C.

In carrying out process variant (a), 1 to 2 moles of acid chloride or acid anhydride of the formula (VI) and, if appropriate, 1 to 2 moles of acid-binding agent are preferably employed per mole of amine derivative of the formula (III). Isolation of the reaction products is effected by customary methods. In general, a procedure is followed in which, when the reaction has ended, the reaction mixture is concentrated, water and an organic solvent are added to the residue, the organic phase is then separated off and, after drying, concentrated and the residue is distilled or recrystallised.

The formula (IV) provides a general definition of the halogenoacylamines required as starting substances in process variant (b). In this formula, $R^1$, $R^2$ and $R^3$ preferably have those meanings which have already been mentioned as preferred in connection with the description of the compounds of the formula (I). $R^6$ represents hydrogen or methyl.

The halogenoacylamines of the general formula

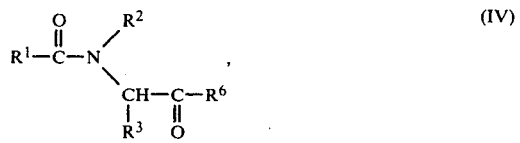

in which
- $R^1$ represents halogenoalkyl,
- $R^2$ represents alkyl, alkenyl, alkynyl, alkoxyalkyl, alkylthioalkyl, aralkyl, halogenoalkyl or alkoximinoalkyl,
- $R^3$ represents hydrogen or alkyl with 1 to 4 carbon atoms and
- $R^6$ represents hydrogen or methyl, have not hitherto been disclosed in the literature.

The halogenoacylamines of the formula (IV) can, however, be prepared in a simple manner. Thus, (c) those halogenoacylamines of the formula (IV) in which $R^6$ represents methyl are obtained by a process in which compounds of the general formula $$R^1-\underset{\underset{O}{\|}}{C}-N\underset{\underset{R^3}{|}}{\overset{R^2}{\diagup}}_{CH-C\equiv CH} \quad (XI)$$

in which $R^1$, $R^2$ and $R^3$ have the meanings indicated above, are treated with water in an acid medium in the presence of a catalyst, or (d) those halogenoacylamines of the formula (IV) in which $R^6$ represents hydrogen are obtained by a process in which acetals of the general formula $$R^1-\underset{\underset{O}{\|}}{C}-N\underset{\underset{R^3}{|}}{\overset{R^2}{\diagup}}_{CH-CH}\underset{O-R^8}{\overset{O-R^7}{\diagup}} \quad (XII)$$

in which
- $R^1$, $R^2$ and $R^3$ have the meanings indicated above,
- $R^7$ represents alkyl and
- $R^8$ represents alkyl, or
- $R^7$ and $R^8$ together represent an ethylene group, are split in the presence of an acid catalyst and in the presence of a diluent.

The formula (XI) provides a general definition of the compounds required as starting substances in process (c). In this formula, $R^1$, $R^2$ and $R^3$ preferably have those meanings which have already been mentioned as preferred for these radicals in connection with the description of the substances of the formula (I).

Some of the compounds of the formula (XI) are known. Those which have not hitherto been described in the literature can, however, be synthesised in a simple manner by processes which are known in principle. Thus, the compounds in question are obtained by a process in which acid chlorides or acid anhydrides of the general formula $$R^1-\underset{\underset{O}{\|}}{C}-X, \quad (II)$$

in which $R^1$ and X have the meanings indicated above, are reacted with alkynylamines of the general formula $$H-N\underset{\underset{R^3}{|}}{\overset{R^2}{\diagup}}_{CH-C\equiv CH} \quad (XVIII)$$

in which $R^2$ and $R^3$ have the meanings indicated above, if appropriate in the presence of an acid-binding agent, for example triethylamine, and if appropriate in the presence of an inert diluent, for example toluene, at temperatures between $-20°$ C. and $100°$ C.

The alkynylamines of the formula (XVIII) are known, or they can be prepared by processes which are known in principle.

Possible catalysts in process (c) are any of the substances which are suitable for such reactions in which water is added onto triple bonds. Mercury sulphate is preferred.

The reaction in process (c) is carried out in an acid medium. Preferred possible reaction media are water-containing acids, for example 85% strength formic acid or half-concentrated sulphuric acid.

The reaction temperatures can be varied within a substantial range in process (c). In general, the reaction is carried out at temperatures between $0°$ C. and $100°$ C., preferably between $20°$ C. and $80°$ C.

Preferably, in carrying out process (c), 1 mole of a compound of the formula (XI) is treated with an excess of aqueous acid in the presence of a catalytic amount of mercury sulphate or of an appropriate catalyst. Working up is effected by customary methods. In general, a procedure is followed in which the reaction mixture is buffered and extracted with an organic solvent which is sparingly soluble in water, the organic phase is neutralised, washed and, after drying, concentrated and the residue is distilled.

The formula (XII) provides a general definition of the acetals required as starting substances in process (d). In this formula, $R^1$, $R^2$ and $R^3$ preferably have those meanings which have already been mentioned as preferred in connection with the description of the halogenoalkylamides of the formula (I). The radicals $R^7$ and $R^8$ each preferably represent alkyl with 1 or 2 carbon atoms. Furthermore, $R^7$ and $R^8$ together can also represent an ethylene group.

The compounds of the formula (XII) are known, or they can be prepared by processes which are known in principle.

Possible catalysts in process (d) are strong organic and inorganic acids. These include, as preferences, sulphuric acid and p-toluenesulphonic acid.

However, it is also possible to use strongly acid ion exchangers containing $-SO_3H$ groups.

Possible diluents in process (d) are water and organic solvents. These include, preferably, toluene and dioxan.

The reaction temperatures can be varied within a substantial range in process (d). In general, the reaction is carried out at temperatures between $20°$ C. and $100°$ C., preferably between $60°$ C. and $100°$ C.

In carrying out process (d), an acetal of the formula (XII) is treated with a catalytic amount of acid in the presence of a diluent. Working up is effected by customary methods.

Formula (V) provides a general definition of the hydroxylamine derivatives also required as starting substances in process (b). In this formula, $R^5$ preferably has those meanings which have already been mentioned as preferred for $R^5$ in connection with the description of the halogenoalkylamides according to the invention.

Possible acid-binding agents in process variant (b) are any of the customary acid acceptors. These include, as preferences, alkali metal acetates, such as sodium acetate and potassium acetate, alkali metal hydroxides, such as sodium hydroxide and potassium hydroxide, alkali metal carbonates, such as sodium carbonate, potassium carbonate and sodium bicarbonate, and lower tertiary amines, such as triethylamine, dimethylbenzylamine, pyridine, diazabicyclooctane and 1,9-diaza-bicyclo[5.4.0]undec-7-ene.

Possible diluents in process variant (b) are water and polar organic solvents. These include, as preferences, alcohols, such as methanol and ethanol; ethers, such as dioxan and tetrahydrofuran; nitriles, such as propionitrile and acetonitrile; and formamides, such as dimethylformamide.

The reaction temperatures can be varied within a substantial range in process variant (b). In general, the reaction is carried out at temperatures between 0° C. and 120° C., preferably between 20° C. and 80° C.

In carrying out process variant (b), 1 to 1.5 moles of hydroxylamine derivative of the formula (V) and 1 to 2 moles of acid-binding agent are preferably employed per mole of halogenoacylamine of the formula (IV). Isolation of the reaction products is effected by customary methods. In general, a procedure is followed in which, when the reaction has ended, the reaction mixture is concentrated, water and an organic solvent which is sparingly soluble in water are added to the residue, the organic phase is separated off, dried and concentrated and the residue is distilled or recrystallised.

As already mentioned, the halogenoalkylamides of the formula (I) are suitable for protecting crop plants from damage by herbicidally active thiolcarbamates and acetanilides, without noticeably influencing the herbicidal action of the compounds.

The halogenoalkylamides of the formula (I) can preferably be used as antidotes for protecting crop plants from damage by herbicidally active thiolcarbamates of the general formula $$R^9-S-\underset{\underset{O}{\|}}{C}-N\diagup_{R^{11}}^{R^{10}} \quad (XIII)$$

in which
$R^9$ represents lower alkyl, benzyl, chlorobenzyl or alkoxybenzyl and
$R^{10}$ and $R^{11}$ independently of one another represent alkyl with 2 to 4 carbon atoms or cyclohexyl, or
$R^{10}$ and $R^{11}$, together with the adjacent nitrogen atom, represent a five-membered to seven-membered heterocyclic ring,
and for protecting crop plants from damage by herbicidally active acetanilides of the general formula (XIV) — structure with phenyl ring bearing $X^1$, $Y^1_n$, and N substituted with $CH_2-R^{12}$ and $CO-CH_2-Z$ in which
$R^{12}$ represents an optionally substituted N-containing heterocyclic radical,
$X^1$ and $Y^1$ are identical or different and represent alkyl,
Z represents halogen and
n represents 0, 1 or 2,
and herbicidally active acid addition salts and metal salt complexes thereof, and of the general formula (XV) — structure with phenyl ring bearing $R^{14}$, $R^{13}_p$, N substituted with $CH(R^{15})$-linked heterocycle containing A and $R^{16}$, and $CO-CH_2-R^{17}$ in which
A represents oxygen, sulphur or the grouping $NR^{18}$,
$R^{15}$ represents hydrogen or alkyl,
$R^{16}$ represents hydrogen, alkyl, halogenoalkyl, alkenyl, alkynyl, cycloalkyl, halogen, optionally substituted aryl, optionally substituted aralkyl or the grouping $-OR^{19}$, $-SR^{19}$ or $NR^{18}R^{19}$,
$R^{18}$ represents hydrogen, alkyl or optionally substituted aryl,
$R^{19}$ represents hydrogen, alkyl, halogenoalkyl, alkenyl, alkynyl, cycloalkyl or optionally substituted aralkyl,
$R^{13}$ represents alkyl,
$R^{14}$ represents alkyl or halogen,
$R^{17}$ represents halogen and
p represents 0, 1 or 2,
and of the formula (XVI) — 2,6-diethylphenyl with N substituted by $CH_2-O-CH_3$ and $CO-CH_2Cl$ and of the formula (XVII) — phenyl with $C_2H_5$ and $CH_3$ ortho substituents, N substituted by $CH(CH_3)-CH_2-OCH_3$ and $CO-CH_2Cl$ The halogenoalkylamides of the formula (I) can also preferably be used as antidotes for protecting crop plants from damage by herbicidally active substituted α-halogenoacetanilides, which are known from DE-OS (German Published Specification) No. 2,918,297.

Specific examples of thiolcarbamates of the formula (XIII) which may be mentioned are: S-ethyl N,N-dipropylthiocarbamate, S-ethyl N,N-diisobutylthiocarbamate, S-propyl N-butyl-N-ethylthiocarbamate, S-propyl N,N-diisopropylthiocarbamate, S-ethyl N,N-diethylthiocarbamate, S-ethyl N-ethyl-N-cyclohexylthiocarbamate, S-ethyl hexahydro-azepine-1-thiocarbamate, S-p-methoxybenzyl N,N-diethylthiocarbamate, S-p-chlorobenzyl N,N-diethylthiocarbamate, S-benzyl N,N-diethylthiocarbamate, S-benzyl N,N-di-sec.-butyl-thiocarbamate and S-propyl N-ethyl-N-butylthiocarbamate.

The thiolcarbamates of the formula (XIII) and their herbicidal activity are already known (see U.S. Pat. Nos. 2,913,327; 3,037,853; 3,185,720; 3,198,786 and 3,582,314).

In the formula (XIV), $R^{12}$ preferably represents an optionally substituted radical selected from pyrazol-1-yl, imidazol-1-yl, 1,2,4-triazol-1-yl, 1,2,3-triazol-1-yl, 1,3,4-triazol-1-yl, 1,2,3,4-tetrazol-1-yl and pyrrol-1-yl. Preferred substituents are: halogen (especially fluorine, chlorine and bromine) and alkyl with 1 to 4 carbon atoms. $X^1$ and $Y^1$ are identical or different and preferably represent straight-chain or branched alkyl with 1 to 4 carbon atoms. Z preferably represents chlorine or bromine and the index n represents 0, 1 or 2.

Specific examples of acetanilides of the formula (XIV) which may be mentioned are: 2-methyl-B 6-ethyl-N-(pyrazol-1-yl-methyl)-chloroacetanilide, 2,6-diethyl-N-(pyrazol-1-yl-methyl)-chloroacetanilide, 2,6-diethyl-N-(1,2,4-triazol-1-yl-methyl)-chloroacetanilide, B 2,6-dimethyl-N-(1,2,4-triazol-1-yl-methyl)-chloroacetanilide, 2-methyl-N-(pyrazol-1-yl-methyl)-chloroacetanilide, 2,5-dimethyl-N-(pyrazol-1-yl-methyl)-chloroacetanilide, 2,3-dimethyl-N-(pyrazol-1-yl-methyl)-chloroacetanilide, 2-methyl-6-ethyl-N-(pyrazol-1-yl-methyl)-chloroacetanilide hydrochloride, 2,6-diethyl-N-(pyrazol-1-yl-methyl)-chloroacetanilide hydrochloride, 2,6-diethyl-N[3,5-dimethyl-pyrazol-1-yl)-methyl]-chloroacetanilide, 2,6-diethyl-N-[(3-chloro-1,2,4-triazolyl)-methyl]-chloroacetanilide, 2-methyl-6-ethyl-N-[(3,5-dimethyl-pyrazol-1-yl)-methyl]-chloroacetanilide, 2-tert.-butyl-N-(pyrazol-1-yl-methyl)-chloroacetanilide, 2-methyl-6-ethyl-N-[(3-bromo-5-methyl-pyrazolyl)-methyl]-chloroacetanilide, 2-methyl-6-ethyl-N-[(3-chloro-1,2,4-triazolyl)-methyl]-chloroacetanilide and 2,6-diethyl-N-[(4-chloro-pyrazol-1-yl)-methyl]-chloroacetanilide.

Further preferred acetanilides of the formula (XIV) are listed by means of their formulae in Table 1 which follows:

TABLE 1

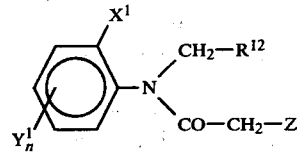
(XIV)

| Example No. | $X^1$ | $Y^1_n$ | Z | $R^{12}$ |
|---|---|---|---|---|
| XIV-1 | $C_2H_5$ | 6-$C_2H_5$ | Cl | Pyrazol-1-yl |
| XIV-2 | $C_2H_5$ | 6-$C_2H_5$ | Cl | 1,2,4-Triazol-1-yl |
| XIV-3 | i-$C_3H_7$ | 6-i-$C_3H_7$ | Cl | Pyrazol-1-yl |
| XIV-4 | $CH_3$ | 6-$C_2H_5$ | Cl | 1,2,4-Triazol-1-yl |
| XIV-5 | $CH_3$ | 6-$C_2H_5$ | Cl | Pyrazol-1-yl |
| XIV-6 | $C_2H_5$ | 4,6-$(CH_3)_2$ | Cl | Pyrazol-1-yl |
| XIV-7 | $CH_3$ | 4,6-$(CH_3)_2$ | Cl | Pyrazol-1-yl |
| XIV-8 | $C_2H_5$ | 4-$CH_3$ | Cl | Pyrazol-1-yl |
| XIV | | 6-$C_2H_5$ | | |
| XIV-9 | i-$C_3H_7$ | 6-i-$C_3H_7$ | Cl | 1,3,4-Triazol-1-yl |
| XIV-10 | i-$C_3H_7$ | 6-i-$C_3H_7$ | Cl | 1,2,4-Triazol-1-yl |
| XIV-11 | $C_2H_5$ | 6-$C_2H_5$ | Cl | Pyrrol-1-yl |
| XIV-12 | i-$C_3H_7$ | — | Cl | 1,2,4-Triazol-1-yl |
| XIV-13 | $CH_3$ | 6-$C_2H_5$ | Cl | 1,2,3,4-Tetrazol-1-yl |
| XIV-14 | i-$C_3H_7$ | — | Cl | Pyrazol-1-yl |
| XIV-15 | $C_2H_5$ | — | Cl | 1,2,4-Triazol-1-yl |
| XIV-16 | $CH_3$ | 6-$CH_3$ | Cl | Pyrazol-1-yl |
| XIV-17 | $CH_3$ | 6-$CH_3$ | Cl | 1,2,4-Triazol-1-yl |
| XIV-18 | $CH_3$ | 5-$CH_3$ | Cl | 1,2,4-Triazol-1-yl |
| XIV-19 | $CH_3$ | — | Cl | Pyrazol-1-yl |
| XIV-20 | $CH_3$ | — | Cl | 1,2,4-Triazol-1-yl |
| XIV-21 | $CH_3$ | 5-$CH_3$ | Cl | Pyrazol-1-yl |
| XIV-22 | $CH_3$ | 3-$CH_3$ | Cl | 1,2,4-Triazol-1-yl |
| XIV-23 | $CH_3$ | 3-$CH_3$ | Cl | Pyrazol-1-yl |
| XIV-24 | $C_2H_5$ | 6-$CH_3$ | Cl | Pyrazol-1-yl (xHCl) |
| XIV-25 | $C_2H_5$ | 6-$C_2H_5$ | Cl | Pyrazol-1-yl (xHCl) |
| XIV-26 | $C_2H_5$ | 6-$C_2H_5$ | Cl | 3,5-Dimethyl-pyrazol-1-yl |
| XIV-27 | $C_2H_5$ | 6-$C_2H_5$ | Cl | Bromomethyl-pyrazol |
| XIV-28 | $C_2H_5$ | 6-$C_2H_5$ | Cl | 3-Chloro-1,2,4-triazol-1-yl |
| XIV-29 | $CH_3$ | 6-$C_2H_5$ | Cl | 3,5-Dimethyl-pyrazol-1-yl |
| XIV-30 | $C_2H_5$ | 6-$C_2H_5$ | Cl | 3-Methyl-pyrazol-1-yl |
| XIV-31 | $C_2H_5$ | 6-$CH_3$ | Cl | 3-Methyl-pyrazol-1-yl |
| XIV-32 | $C(CH_3)_3$ | — | Cl | Pyrazol-1-yl |
| XIV-33 | $C(CH_3)_3$ | — | Cl | 1,2,4-Triazol-1-yl |
| XIV-34 | $C_2H_5$ | 6-$CH_3$ | Cl | Bromo-methyl-pyrazolyl |
| XIV-35 | $CH_3$ | 6-$C_2H_5$ | Cl | 4-Chloro-pyrazol-1-yl |
| XIV-36 | $CH_3$ | 6-$C_2H_5$ | Cl | 3-Chloro-1,2,4-triazol-1-yl |
| XIV-37 | $C_2H_5$ | 6-$CH_3$ | Cl | 2,4,5-Trichloro-imidazol-1-yl |
| XIV-38 | $C_2H_5$ | 6-$C_2H_5$ | Cl | 4-Chloro-pyrazol-1-yl |
| XIV-39 | $C_2H_5$ | 6-$C_2H_5$ | Cl | 1,2,3,4-Tetrazol-1-yl |
| XIV-40 | $C_2H_5$ | 6-$C_2H_5$ | Br | Pyrazol-1-yl |
| XIV-41 | $CH_3$ | 6-$C_2H_5$ | Br | Pyrazol-1-yl |
| XIV-42 | $C_2H_5$ | 6-$C_2H_5$ | Cl | Imidazol-1-yl |
| XIV-43 | $C_2H_5$ | 6-$C_2H_5$ | Br | 1,2,4-Triazol-1-yl |
| XIV-44 | $CH_3$ | 6-$C_2H_5$ | Br | 1,2,4-Triazol-1-yl |

The acetanilides of the formula (XIV) and their herbicidal activity, and herbicidally active acid addition salts and metal salt complexes thereof are already known (see DE-OS (German Published Specification) No. 2,648,088 and DE-OS (German Published Specification) No. 2,704,281).

In the formula (XV), A preferably represents oxygen, sulphur or the grouping —$NR^{18}$, wherein $R^{18}$ represents hydrogen, straight-chain or branched alkyl with 1 to 4 carbon atoms or aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine and chlorine). $R^{15}$ preferably represents hydrogen or methyl. $R^{16}$ in the formula (XV)

preferably represents hydrogen, straight-chain or branched alkyl with 1 to 4 carbon atoms, halogenoalkyl with up to 3 carbon atoms and up to 5 identical or different halogen atoms (preferred halogens being fluorine and chlorine, and trifluoromethyl being mentioned as an example), alkenyl or alkynyl with in either case 2 to 4 carbon atoms, cycloalkyl with 5 to 7 carbon atoms or halogen (especially fluorine, chlorine or bromine). $R^{16}$ furthermore preferably represents aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine and chlorine, and trifluoromethyl being mentioned as a specific example of halogenoalkyl). $R^{16}$ furthermore preferably represents aralkyl with 6 to 10 carbon atoms in the aryl part and 1 to 4 carbon atoms in the alkyl part (especially benzyl), it being possible for the aralkyl radical to carry, on the aryl part, one or more substituents selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine, and trifluoromethyl being mentioned as a specific example of halogenoalkyl). $R^{16}$ also represents the grouping $-OR^{19}$, $-SR^{19}$ or $-NR^{18}R^{19}$, wherein $R^{18}$ has the preferred meaning which has already been mentioned above for this radical, and $R^{19}$ represents hydrogen, straight-chain or branched alkyl with 1 to 4 carbon atoms, halogenoalkyl with 1 to 3 carbon atoms and up to 5 identical or different halogen atoms (preferred halogens being fluorine and chlorine, and trifluoromethyl being mentioned as an example), alkenyl or alkynyl with in either case 2 to 4 carbon atoms, cycloalkyl with 5 to 7 carbon atoms or aralkyl with 6 to 10 carbon atoms in the aryl part and 1 to 4 carbon atoms in the alkyl part (especially benzyl), it being possible for the aralkyl radical to carry, on the aryl part, one or more substituents selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine, and trifluoromethyl being mentioned as a specific example of halogenoalkyl). In the formula (XV), $R^{13}$ preferably represents straight-chain or branched alkyl with 1 to 4 carbon atoms, $R^{14}$ preferably represents straight-chain or branched alkyl with 1 to 4 carbon atoms, fluorine, chlorine or bromine and $R^{17}$ preferably represents chlorine, bromine or iodine. The index p represents 0, 1 or 2.

Specific examples of acetanilides of the formula (XV) which may be mentioned are: 2,6-diethyl-N-[(2-methyl-1,3,4-oxadiazol-5-yl)-methyl]-chloroacetanilide, 2,6-dimethyl-N-[(2-methyl-1,3,4-oxadiazol-5-yl)-methyl]-chloroacetanilide, 2-ethyl-6-methyl-N-[(2-methyl-1,3,4-oxadiazol-5-yl)-methyl]-chloroacetanilide and 2-tert.-butyl-N-[(2-methyl-1,3,4-oxadiazol-5-yl)-methyl]-chloroacetanilide.

Further preferred possible acetanilides of the formula (XV) are listed by means of their formulae in Table 2 which follows.

TABLE 2

(XV)

| Example No. | $R^{15}$ | $R^{16}$ | $R^{14}$ | $R^{13}_p$ | A | $R^{17}$ |
|---|---|---|---|---|---|---|
| XV-1 | H | CH$_3$ | CH$_3$ | 6-C$_2$H$_5$ | O | Cl |
| XV-2 | H | SCH$_3$ | C$_2$H$_5$ | 6-C$_2$H$_5$ | N—CH$_3$ | Cl |
| XV-3 | H | CH$_3$ | C$_2$H$_5$ | 6-C$_2$H$_5$ | O | Cl |
| XV-4 | H | CH$_3$ | CH$_3$ | 6-CH$_3$ | O | Cl |
| XV-5 | H | CH$_3$ | C(CH$_3$)$_3$ | — | O | Cl |
| XV-6 | H | —S—CH$_2$—CH=CH$_2$ | C$_2$H$_5$ | 6-C$_2$H$_5$ | \>N–CH$_3$ | Cl |
| XV-7 | H |  | CH$_3$ | 6-C$_3$H$_5$ | \>N–CH$_3$ | Cl |
| XV-8 | H | C$_2$H$_5$ | CH$_3$ | 6-C$_2$H$_5$ | O | Cl |
| XV-9 | H | C$_2$H$_5$ | C$_2$H$_5$ | 6-C$_2$H$_5$ | O | Cl |
| XV-10 | H | i-C$_3$H$_7$ | CH$_3$ | 6-C$_2$H$_5$ | O | Cl |
| XV-11 | H | CH$_3$ | CH$_3$ | 3-CH$_3$ |  | Cl |
| XV-12 | H | CH$_3$ | C$_2$H$_5$ | 6-C$_2$H$_5$ | O | Br |
| XV-13 | H | CH$_3$ | CH$_3$ | 6-C$_2$H$_5$ | O | Br |

TABLE 2-continued

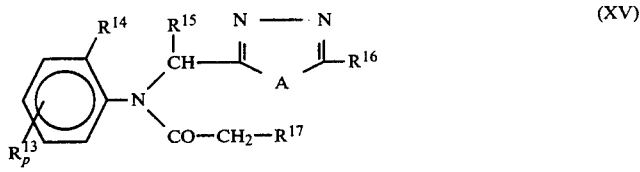

| Example No. | R¹⁵ | R¹⁶ | R¹⁴ | R¹³ₚ | A | R¹⁷ |
|---|---|---|---|---|---|---|
| XV-14 | H | CH₃ | i-C₃H₇ | 6-i-C₃H₇O | | Cl |

The acetanilides of the formula (XV) and their herbicidal activity are already known (see DE-OS (German Published Specification) No. 2,805,757).

Further preferred possible acetanilides with which the compounds of the formula (I) according to the invention can be employed as antidotes are the compounds of the formulae (XVI) and (XVII). These substances and their herbicidal activity are already known (see U.S. Pat. No. 3,442,945 and DE-OS (German Published Specification) No. 2,328,340).

The halogenoalkylamides of the formula (I) according to the invention are particularly suitable for protecting important crop plants, such as maize, soya bean, cotton, sugar beet, cereals, rice and cane sugar, from herbicidal damage by thiolcarbamates and acetanilides.

The active compound combinations according to the invention, comprising (a) a halogenoalkylamide of the formula (I) and (b) at least one herbicidally active thiolcarbamate and/or at least one herbicidally active acetanilide, exhibit a very good action against broad-leaved weeds and gramineous weeds in numerous crops of useful plants. They can therefore be used for selectively combating weeds in numerous crops of useful plants. By weeds, in the broadest sense, there are to be understood in this context all plants which grow in locations where they are undesired.

The active compound combinations according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound combinations according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

The active compound combinations according to the invention are particularly suitable for selectively combating weeds in maize, soya beans, cotton, sugar beet, cereals, rice and cane sugar.

The antidotes according to the invention can be converted, if appropriate as a mixture with the herbicidal active compounds with which they are employed, into the customary formulations, such as solutions, emulsions, wettable powders, suspensions, powders, dusting agents, foams, soluble powders, granules, suspension-emulsion concentrates, natural and synthetic materials impregnated with active compound, very fine capsules in polymeric substances and in coating compositions for seed.

These formulations are produced in known manner, for example by mixing the antidotes according to the invention, if appropriate as a mixture with the herbicidal active compounds with which they are employed, with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain between 0.1 and 95% by weight of antidote or antidote and herbicidal active compound, preferably between 0.5 and 90%.

The antidotes according to the invention can also be employed, as such or in the form of their formulations, as mixtures with herbicidal active compounds, finished formulations or tank mixing being possible. Mixtures with other active compounds, such as fungicides, insecticides, acaricides, nematicides, bird repellants, growth factors, plant nutrients and agents which improve soil structure are also possible.

The antidotes according to the invention or mixtures of an antidote according to the invention and a herbicidal active compound can be employed as such, in the form of their formulations or in the use forms prepared therefrom by further dilution, such as ready-to-use solutions, suspensions, emulsions, powders and granules. They may be used in the customary manner, for example by watering, spraying, atomising, dusting or scattering, dry dressing, moist dressing, wet dressing, slurry dressing or encrusting.

The antidotes according to the invention can be applied by methods customary for antidotes of this type. Thus, the antidotes according to the invention can be applied either before or after the herbicide, or can be applied together with the herbicide. If the herbicide is used before or after sowing, crop plants can also be protected against damage by treating the seed with the antidotes before sowing (dressing). A further possible way of using the antidotes is to apply them to the seed furrow during sowing. If the plants are seedlings, these can be treated with the antidotes before being transplanted.

When the antidotes according to the invention are employed, the customary amounts, at the location, of the particular herbicides are applied. The amounts of herbicidal active compound used vary between 0.5 and 5 kg/ha. The amount of antidote used is independent of the herbicide and of the amount of herbicidal active compound used. In general, the amounts of antidotes according to the invention applied are between 0.1 and 5 kg/ha in the case of treatment of the soil surface, preferably between 0.2 and 4 kg/ha. In the case of seed treatment, the amounts of antidotes according to the invention applied are in general between 10 and 300 g per kilogram of seed, preferably between 25 and 200 g per kilogram of seed.

The weight ratios of antidotes to herbicidal active compounds in the active compound combinations according to the invention can vary within relatively wide limits. In general, 0.04 to 1.0 part by weight, preferably 0.1 to 0.5 part by weight, of antidote of the formula (I) is present per 1 part by weight of herbicidal active compound.

Thus, the present invention also provides an antidote composition containing as active ingredient a compound of the formula (I) in admixture with a solid diluent or carrier or in admixture with a liquid diluent or carrier containing a surface-active agent.

The present invention also provides a method of protecting crop plants from damage by herbicidally active thiolcarbamates or herbicidally active acetanilides, in which there is applied to the plants, or to a habitat thereof, a compound of the formula (I) alone or in the form of a composition containing as active ingredient a compound of the formula (I) in admixture with a diluent or carrier.

The present invention also provides crops protected from damage by herbicidally active thiolcarbamates or by herbicidally active acetanilides by being grown in areas in which immediately prior to and/or during the time of the growing a compound of the formula (I) was applied, alone or in admixture with a diluent or carrier.

The present invention also provides a herbicidal composition that contains as active ingredients (1) a compound of the formula (I) and (2) at least one herbicidally active compound selected from thiolcarbamates and acetanilides, alone or in admixture with a solid or liquid diluent or carrier.

The present invention also provides a method of combating weeds, in which there is applied to the weeds, or to a habitat thereof, a herbicidal composition according to the present invention.

The present invention further provides crops protected from damage by weeds by being grown in areas in which immediately prior to and/or during the time of the growing, a herbicidal composition of the present invention was applied.

It will be seen that the usual methods of providing a harvested crop may be improved by the present invention.

The preparation of the halogenoalkylamides according to the invention is illustrated in the following examples.

PREPARATIVE EXAMPLES

EXAMPLE 1

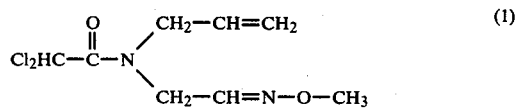

(1)

88.4 g (0.6 mol) of dichloroacetic acid chloride were added dropwise to a solution of 75 g (0.58 mol) of allyl-2-methoximino-ethylamine and 60.6 g (0.6 mol) of triethylamine in 500 ml of tetrahydrofuran at 5° to 10° C., whilst stirring. The mixture was subsequently stirred for a further hour at 20° C. It was then worked up by stripping off the solvent, taking up the residue in water and methylene chloride and separating off the organic phase, drying it over sodium sulphate and concentrating it. The residue was distilled under reduced pressure. 133.5 g (95% of theory) of N-allyl-N-(2-methoximino-ethyl)-dichloroacetamide were obtained in this manner. Boiling point=150° C./0.1 mm Hg (bulb tube).

Preparation of the starting material

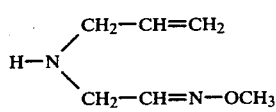  (III-1)

150 g (1.4 mol) of chloroacetaldehyde-oxime O-methyl ether were added dropwise to a mixture of 239 g (4.2 mol) of allylamine and 192 g (1.4 mol) of powdered potassium carbonate at 50° C., whilst stirring. When the exothermic reaction had ended, the mixture was stirred for a further 2 hours at 50° C. The precipitate was then filtered off and the filtrate was subjected to fractional vacuum distillation. 132.9 g (74% of theory) of allyl-2-methoximinoethyl-amine were obtained in this manner. Boiling point = 62°–64° C./12 mm Hg.

A further 10.3 g of a product passed over at 107° C./12 mm Hg; the spectroscopic data proved that the product was the bisalkylation product of the formula

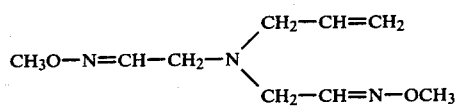

EXAMPLE 2

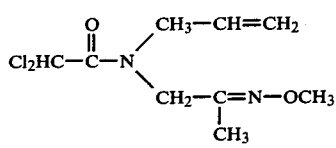  (2)

3.5 g (0.015 mol) of N-2-oxo-propyl-N-allyl-dichloroacetic acid amide were added to a boiling mixture of 1.7 g of anhydrous sodium acetate and 1.7 g (0.02 mol) of O-methyl-hydroxylamine hydrochloride in 100 ml of ethanol. The mixture was boiled under reflux for one hour. It was then worked up by concentrating under reduced pressure, taking up the residue in water and methylene chloride and separating off the organic phase, drying it over sodium sulphate and then concentrating it. 3.7 g (97% of theory) of N-(2-methoximinopropyl)-N-allyl-dichloroacetic acid amide were obtained in this manner. $n_D^{20} = 1.5008$.

Preparation of the starting material

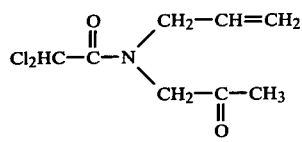  (IV-1)

10 g (0.049 mol) of dichloroacetic acid N-allyl-N-propargylamide were added dropwise to a mixture, heated to 80° C., of 80 ml of 85% strength formic acid and 1 g of mercury sulphate, whilst stirring. The mixture was subsequently stirred for 12 hours, cooled and, after adding 50 ml of saturated aqueous ammonium sulphate solution, extracted three times with methylene chloride. After neutralising the organic phase with aqueous sodium carbonate solution, it was washed twice more with 50 ml of water each time and dried over sodium sulphate. After distilling off the solvent, the residue was distilled under reduced pressure. 5.5 g (50% of theory) of N-2-oxo-propyl-N-allyl-dichloroacetic acid amide were obtained in this manner. Boiling point = 135° C./0.2 mm Hg (bulb tube); $n_D^{20} = 1.5033$.

Preparation of the precursor

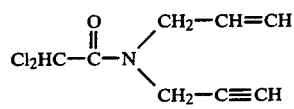

13 g (0.13 mol) of allylpropargylamine and 14.2 g (0.14 mol) of triethylamine were dissolved in 150 ml of tetrahydrofuran, and 20.6 g (0.14 mol) of dichloroacetic acid chloride were added dropwise at 5°–10° C., whilst stirring. The mixture was subsequently stirred for a further 2 hours at 20° C. The solvent was then stripped off and water and methylene chloride were added to the residue. The organic phase was separated off and dried over sodium sulphate, the solvent was stripped off and the residue was distilled under reduced pressure. 17 g (63% of theory) of dichloroacetic acid N-allyl-N-propargylamide were obtained in this manner. Boiling point = 85°–87° C./0.2 mm Hg; $n_D^{20} = 1.5139$.

The halogenoalkylamides of the formula (I) listed by means of their formulae in Table 3 which follows were prepared by methods analogous to those indicated in Examples 1 and 2.

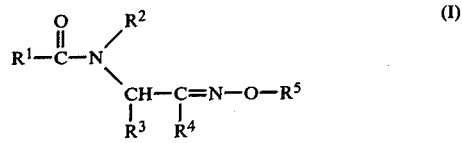  (I)

TABLE 3

| Example No. | $R^1$ | $R^2$ | $R^3$ | $R^4$ | $R^5$ | Refractive index $[n_D^{20}]$ |
|---|---|---|---|---|---|---|
| 3 | Cl$_2$HC— | CH$_3$ | H | CH$_3$ | CH$_3$ | 1.5003 |
| 4 | ClHC—<br>\|<br>CH$_3$ | —CH$_2$—CH=CH$_2$ | H | CH$_3$ | CH$_3$ | 1.4868 |
| 5 | Cl$_2$HC— | —CH$_2$—CH=CH$_2$ | CH$_3$ | H | CH$_3$ | 1.5022 |

TABLE 3-continued

| Example No. | R¹ | R² | R³ | R⁴ | R⁵ | Refractive index [$n_D^{20}$] |
|---|---|---|---|---|---|---|
| 6 | $Cl_2HC-$ | $-CH_2-CH=CH_2$ | H | H | $C_2H_5$ | |
| 7 | $Cl_2HC-$ | $-CH_2-CH=CH_2$ | H | $CH_3$ | $C_2H_5$ | |
| 8 | $ClHC-$<br>\|<br>$CH_3$ | $-CH_2-CH=CH_2$ | H | H | $CH_3$ | 1.4873 |
| 9 | $Cl_2CH-$ | $\quad\quad CH_3$<br>$\quad\quad\|$<br>$-CH_2-C=N-OCH_3$ | H | $CH_3$ | $CH_3$ | 1.4870 |
| 10 | $Cl_2CH-$ | $-CH_2-CH=CH_2$ | $CH_3$ | $CH_3$ | $CH_3$ | |

The substances listed by means of their formulae in Table 4 which follows were prepared in an analogous manner to the starting material (IV-1) described in Example 2:

TABLE 4

$$R^1-\overset{O}{\underset{\|}{C}}-N\overset{R^2}{\underset{\underset{R^3\ R^6}{\underset{|\ \ |}{CH-C=O}}}{}} \quad (IV)$$

| Example No. | R¹ | R² | R³ | R⁶ | $n_D^{20}$ or melting point |
|---|---|---|---|---|---|
| IV-2 | $Cl_2CH-$ | $-CH_2-CH=CH_2$ | H | $CH_3$ | 1.5033 |
| IV-3 | $CH_3-CH-$<br>\|<br>$Cl$ | $-CH_2-CH=CH_2$ | H | $CH_3$ | 1.4869 |
| IV-4 | $Cl_2CH-$ | $-CH_3$ | H | $CH_3$ | 1.5015 |
| IV-5 | $Cl_2CH-$ | $\quad O$<br>$\quad \|\|$<br>$CH_2-C-CH_3$ | H | $CH_3$ | 111° C. |
| IV-6 | $Cl_2CH-$ | $-CH_2-CH=CH_2$ | H | H | (melting point) |
| IV-7 | $Cl_2CH-$ | $-CH_2-CH=CH_2$ | $CH_3$ | $CH_3$ | |

The antidote activity of the compounds of this invention is illustrated by the following biotest Example.

In this Example, the compounds according to the present invention are each identified by the number (given in brackets) of the corresponding preparative Example.

The known comparison compound is identified as follows:

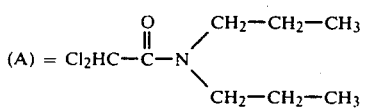

(N,N-Di-n-propyl-dichloroacetamide)

Furthermore, the acetanilide indicated below is employed as the herbicidal active compound in this example.

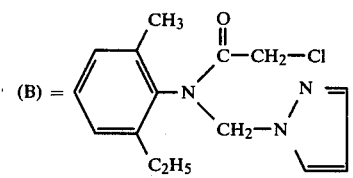

(2-Methyl-6-ethyl-N-(pyrazol-1-yl)-methyl)-chloroacetanilide).

EXAMPLE A

Pre-emergence test

Solvent: 5 parts by weight of acetone
Emulsifier: 1 part by weight of alkylaryl polyglycol ether To produce a suitable preparation of active compound, 1 part by weight of herbicidal active compound or antidote, or of a mixture of antidote and herbicidal active compound, was mixed with the stated amount of solvent, the stated amount of emulsifier was added and the concentrate was diluted with water to the desired concentration.

Seeds of the test plants were sown in normal soil and, after 24 hours, watered with the herbicide preparation or antidote preparation or with the preparation of antidote and herbicidal active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

Evaluation of the test results showed that compounds (1) and (4) were more suitable for protecting crop plants from damage by 2-methyl-6-ethyl-N-(pyrazol-1-yl-methyl)-chloro-acetanilide than the comparison component (A).

It will be understood that the specification and examples are illustrative, but not limitative of the present invention and that other embodiments within the spirit and scope of the invention will suggest themselves to those skilled in the art.

What is claimed is:
1. Haloalkylamide compound of the formula

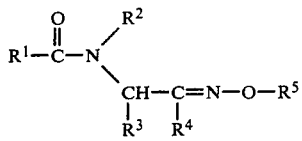

wherein
R[1] is haloalkyl;
R[2] is alkyl, alkenyl, alkynyl, alkoxyalkyl, alkylthioalkyl, haloalkyl or alkoximinoalkyl;
R[3] is hydrogen or alkyl with 1 to 4 carbon atoms;
R[4] is hydrogen or alkyl with 1 to 4 carbon atoms; and
R[5] is hydrogen, alkyl, alkenyl, alkynyl or aralkyl.

2. Haloalkylamide compound as claimed in claim 1 wherein R[1] is haloalkyl with 1 to 4 carbon atoms and 1 to 3 halogen atoms.

3. Haloalkylamide compound as claimed in claim 1 wherein R[2] is alkyl with 1 to 6 carbon atoms.

4. Haloalkylamide compound as claimed in claim 1 wherein R[2] is alkenyl with up to 6 carbon atoms.

5. Haloalkylamide compound as claimed in claim 1 wherein R[2] is alkynyl with up to 6 carbon atoms.

6. Haloalkylamide compound as claimed in claim 1 wherein R[2] is alkoxyalkyl with from 1 to 4 carbon atoms in the alkyl moiety and 1 to 4 carbon atoms in the alkoxy moiety.

7. Haloalkylamide compound as claimed in claim 1 wherein R[2] is alkylthioalkyl with 1 to 4 carbon atoms in the alkyl moiety and 1 to 4 carbon atoms in the alkylthio moiety.

8. Haloalkylamide compound as claimed in claim 1 wherein R[2] is haloalkyl with from 1 to 6 carbon atoms and 1 to 5 halogen atoms.

9. Haloalkylamide compound as claimed in claim 1 wherein R[2] is alkoximinoalkyl with from 1 to 4 carbon atoms in the alkoxy group and 1 to 2 carbon atoms in the alkyl group.

10. Haloalkylamide compound as claimed in claim 1 wherein R[3] is hydrogen.

11. Haloalkylamido compound as claimed in claim 1 wherein R[3] is methyl.

12. Haloalkylamido compound as claimed in claim 1 wherein R[3] is ethyl.

13. Haloalkylamido compound as claimed in claim 1 wherein R[4] is hydrogen.

14. Haloalkylamido compound as claimed in claim 1 wherein R[4] is methyl.

15. Haloalkylamido compound as claimed in claim 1 wherein R[4] is ethyl.

16. Haloalkylamido compound as claimed in claim 1 wherein R[5] is hydrogen.

17. Haloalkylamido compound as claimed in claim 1 wherein R[5] is alkyl with from 1 to 6 carbon atoms.

18. Haloalkylamido compound as claimed in claim 1 wherein R[5] is alkenyl with up to 6 carbon atoms.

19. Haloalkylamido compound as claimed in claim 1 wherein R[5] is alkynyl with up to 6 carbon atoms.

20. Haloalkylamide compound as claimed in claim 1 wherein R[5] is aralkyl with from 6 to 10 carbon atoms in the aryl moiety and from 1 to 4 carbon atoms in the alkyl moiety.

21. Haloalkylamide compound as claimed in claim 1 wherein
R[1] is straight-chain or branched haloalkyl with 1 to 4 carbon atoms and 1 to 3 halogen atoms;
R[2] is straight-chain or branched alkyl with 1 to 6 carbon atoms, alkenyl with up to 6 carbon atoms, alkynyl with up to 6 carbon atoms, alkoxyalkyl with 1 to 4 carbon atoms in the alkyl group and 1 to 4 carbon atoms in the alkoxy part, alkylthioalkyl with 1 to 4 carbon atoms in the alkyl part and 1 to 4 carbon atoms in the alkylthio part, aralkyl with 6 to 10 carbon atoms in the aryl part and 1 to 4 carbon atoms in the alkyl part, haloalkyl with 1 to 6 carbon atoms and 1 to 5 halogen atoms, or alkoximinoalkyl with 1 to 4 carbon atoms in the alkoxy group and 1 or 2 carbon atoms in the alkyl group;
R[3] is hydrogen, methyl or ethyl;
R[4] is hydrogen, methyl or ethyl; and
R[5] is hydrogen, straight-chain or branched alkyl with 1 to 6 carbon atoms, alkenyl with up to 6 carbon atoms, alkynyl with up to 6 carbon atoms or aralkyl with 6 to 10 carbon atoms in the aryl part and 1 to 4 carbon atoms in the alkyl part.

22. Haloalkylamide compound as claimed in claim 1 wherein
R[1] is haloalkyl with 1 to 3 carbon atoms and 1 to 3 chlorine or bromine atoms;
R[2] is alkyl with 1 to B 4 carbon atoms, alkenyl with up to 4 carbon atoms, alkynyl with up to 4 carbon atoms, alkoxyalkyl with 1 to 3 carbon atoms in the alkoxy group and 1 to 4 carbon atoms in the alkyl part, alkylthioalkyl with 1 to 3 carbon atoms in the alkylthio part and 1 to 3 carbon atoms in the alkyl part, aralkyl with 6 to 10 carbon atoms in the aryl part and 1 or 2 carbon atoms in the alkyl part, haloalkyl with 1 to 4 carbon atoms and 1 to 3 halogen atoms selected from fluorine, chlorine and bromine atoms, or alkoximinoalkyl with 1 to 3 carbon atoms in the alkoxy group and 1 or 2 carbon atoms in the alkyl group;
R[3] is hydrogen, methyl or ethyl;
R[4] is hydrogen, methyl or ethyl; and
R[5] is hydrogen, alkyl with 1 to 4 carbon atoms, alkenyl with up to 4 carbon atoms, alkynyl with up to 4 carbon atoms or aralkyl with 6 to 10 carbon atoms in the aryl part and 1 or 2 carbon atoms in the alkyl part.

23. Haloalkylamide compound as claimed in claim 1 designated N-allyl-N-(2-methoximino-ethyl)-dichloroacetamide.

24. Haloalkylamide compound as claimed in claim 1 designated N-allyl-N-(2-methoximino-propyl)-dichloroacetamide.

25. Haloalkylamide compound as claimed in claim 1 designated N-methyl-N-(2-methoximino-propyl)-dichloroacetamide.

26. Haloalkylamide compound as claimed in claim 1 designated N-allyl-N-(2-methoximino-propyl)-2-chloropropionamide.

27. An antidote composition for protecting crop plants from herbicidal damage by herbicidally active acetanilides comprising as an active ingredient an antidotal amount of at least one haloalkylamide compound as claimed in claim 1, in admixture with a solid diluent or with a liquid diluent containing a surfactant.

28. An antidote composition as claimed in claim 27 containing from 0.1 to 95% of the said compound by weight.

29. Method for the protection of crop plants from damage by herbicidally active acetanilides, which method comprises applying to the plants or their habitat an antidotally effective amount of a haloalkylamide compound as claimed in claim 1.

30. Method of claimed in claim 29 wherein said compound is applied to an area of agriculture in an amount of from 0.1 to 5 kg per hectare.

31. Method as claimed in claim 29 wherein said compound is applied to seen in an amount of 10 to 300 grams per kg of seed.

32. Herbicidal composition comprising a herbicidally active compound selected from thiolcarbamates and acetanilide herbicides and, as an antidote, an effective amount of a haloalkylamide compound as claimed in claim 1.

33. Herbicidal composition as claimed in claim 32 wherein said herbicidally active compound is a thiolcarbamate.

34. Herbicidal composition as claimed in claim 32 wherein said herbicidally active compound is an acetanilide.

35. Herbicidal composition as claimed in claim 32 containing from 0.1 to 95% of the combination of said antidote compound and said herbicide, by weight.

36. Herbicidal composition as claimed in claim 32 containing from 0.04 to 1 part by weight of said antidote compound per part by weight of said herbicidally active compound.

37. Herbicidal composition as claimed in claim 32 containing from 0.1 to 0.5 part by weight of said antidote compound per part by weight of said herbicidally active compound.

38. Method of combating weeds comprising applying to the weeds or their habitat a composition as claimed in claim 32.

39. Method as claimed in claim 38 wherein the composition is applied at a rate corresponding to 0.5 to 5 kg per hectare of said herbicidally active compound.

40. Method as claimed in claim 29 wherein said antidotal compound is selected from
   N-allyl-N-(2-methoximino-ethyl)-dichloroacetamide;
   N-allyl-N-(2-methoximino-propyl)-dichloroacetamide;
   N-methyl-N-(2-methoximino-propyl)-dichloroacetamide; or
   N-allyl-N-(2-methoximino-propyl)-2-chloropropanamide.

41. Herbicidal composition as claimed in claim 32 wherein said antidotal compound is selected from
   N-allyl-N-(2-methoximino-ethyl)-dichloroacetamide;
   N-allyl-N-(2-methoximino-propyl)-dichloroacetamide;
   N-methyl-N-(2-methoximino-propyl)-dichloroacetamide; or
   N-allyl-N-(2-methoximino-propyl)-2-chloropropanamide.

42. Method as claimed in claim 38 wherein said antidotal compound is selected from
   N-allyl-N-(2-methoximino-ethyl)-dichloroacetamide;
   N-allyl-N-(2-methoximino-propyl)-dichloroacetamide;
   N-methyl-N-(2-methoximino-propyl)-dichloroacetamide; or
   N-allyl-N-(2-methoximinopropyl)-2-chloropropanamide.

* * * * *